United States Patent

Better et al.

[11] Patent Number: 5,264,651
[45] Date of Patent: Nov. 23, 1993

[54] METHOD FOR REGENERATING HF/SULFOLANE ALKYLATION CATALYST

[75] Inventors: Michael A. Better, Deptford; Jonathan E. Child; Tomas R. Melli, both of Sewell, all of N.J.; Sergei Yurchak, Media, Pa.

[73] Assignee: Mobil Oil Corporation, Fairfax, Va.

[21] Appl. No.: 991,920

[22] Filed: Dec. 17, 1992

Related U.S. Application Data

[63] Continuation-in-part of Ser. No. 833,684, Feb. 11, 1992, Pat. No. 5,191,150.

[51] Int. Cl.⁵ .................. C07C 2/62; C07C 7/10
[52] U.S. Cl. .................. 585/802; 585/723; 585/724; 585/857
[58] Field of Search .................. 585/723, 724, 802, 857

[56] References Cited

U.S. PATENT DOCUMENTS

| | | | |
|---|---|---|---|
| 3,795,712 | 3/1974 | Torck et al. | 585/724 |
| 4,014,953 | 3/1977 | Brown, Jr. | 585/724 |
| 4,058,575 | 11/1977 | Cahn et al. | 585/724 |
| 4,199,409 | 4/1980 | Skraba | 585/724 |
| 4,317,795 | 3/1982 | Makovec et al. | 422/62 |
| 4,663,026 | 5/1987 | Louie et al. | 585/723 |
| 5,191,150 | 3/1993 | Child et al. | 585/809 |

Primary Examiner—Asok Pal
Attorney, Agent, or Firm—Alexander J. McKillop; Dennis P. Santini; Robert B. Furr, Jr.

[57] ABSTRACT

This invention provides a method for separating ASO from a mixture containing ASO, HF and sulfolane comprising the steps of:
(a) contacting said mixture with a sorbent to selectively sorb HF and water from said mixture to evolve an intermediate product containing less than 5 weight percent HF;
(b) charging said intermediate product to a gravitational separation zone;
(c) holding said intermediate product in said gravitational separation zone for time sufficient to evolve two at least partially immiscible liquid phases in said gravitational separation zone; and
(d) withdrawing a less-dense phase enriched in ASO and a more-dense phase enriched in sulfolane from said gravitational separation zone.

8 Claims, 1 Drawing Sheet

SULFOLANE PURIFICATION UTILIZING HF ADSORPTION

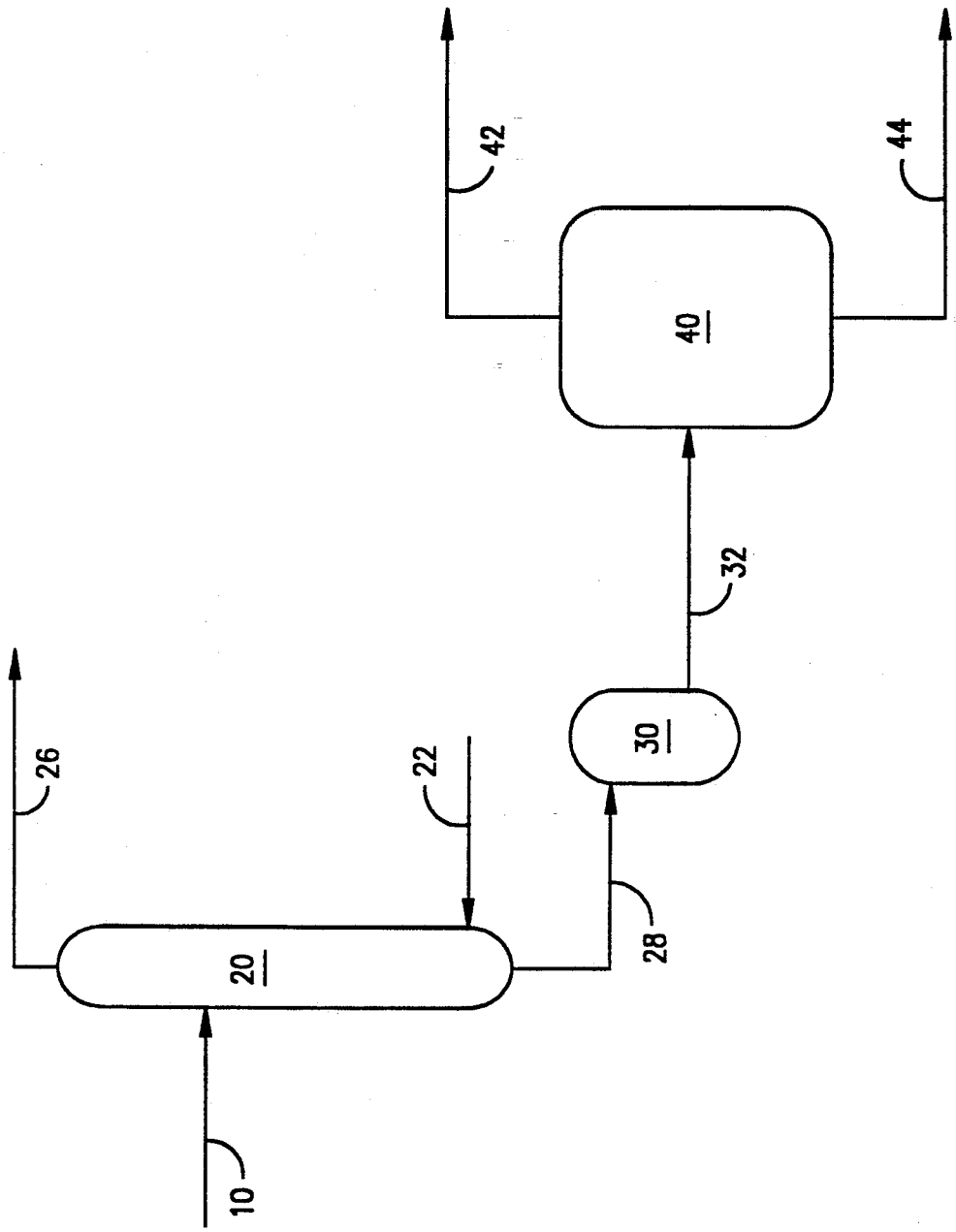

METHOD FOR REGENERATING HF/SULFOLANE ALKYLATION CATALYST

CROSS REFERENCE TO RELATED APPLICATIONS

This is a continuation-in-part of application Ser. No. 07/833,684, filed Feb. 11, 1992, now U.S. Pat. No. 5,191,150.

This application is related by disclosure of similar subject matter to Ser. No. 07/991,918. filed Dec. 17, 1992, Ser. No. 07/991,919, filed Dec. 17, 1992, Ser. No. 07/991,921, filed Dec. 17, 1992, and Ser. No. 07/991,922, filed Dec. 17, 1992, filed on even date herewith now all allowed.

FIELD OF THE INVENTION

The present invention relates to the art of catalytic alkylation. More specifically, the invention relates to a method for regenerating a liquid alkylation catalyst. Particularly, the invention provides a method for removing conjunct polymeric byproducts from a mixture of HF and sulfolane.

BACKGROUND OF THE INVENTION

Recent regulatory developments have led refiners to seek methods for reformulating motor gasolines to meet increasingly stringent air quality requirements. These techniques include reducing the olefin and aromatic content of the motor gasoline while maintaining the desired octane rating by increasing the relative content of isooctane (trimethylpentane) and other octane-enhancing additives such as oxygenates.

Commercial isobutane-butene alkylation, catalyzed by a strong mineral acid such as HF or $H_2SO_4$, produces a highly desirable motor gasoline blending component which is enriched in high-octane trimethylpentane. Thus with the advent of more restrictive air quality regulations, the known commercial isobutane-butene alkylation processes present a seemingly ideal solution to the problem of reformulating motor gasoline to minimize both evaporative losses from storage as well as pollutants emissions from gasoline engine operations.

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used large volumes of liquid Bronsted acid catalysts such as hydrofluoric or sulfuric acid under relatively low temperature conditions. Acid strength is preferably maintained at 88 to 94 weight percent by the continuous addition of fresh acid and the continuous withdrawal of spent acid. Liquid acid catalyzed isoparaffin-olefin alkylation processes share inherent drawbacks including environmental and safety concerns, acid consumption, and sludge disposal. For a general discussion of sulfuric acid alkylation, see the series of three articles by L.F. Albright et al., "Alkylation of Isobutane with $C_4$ Olefins," 27 *Ind. Eng. Chem. Res.*, 381-397, (1988). For a survey of hydrofluoric acid catalyzed alkylation, see 1 *Handbook of Petroleum Refining Processes* 23-28 (R.A. Meyers, ed., 1986).

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids, and alternatives such as Lewis acids, e.g., $BF_3$, have been explored. While Lewis acids generally pose fewer and less severe safety and environmental concerns than strong liquid acids such as HF and $H_2SO_4$, it would be desirable to produce paraffin-rich product streams useful as gasoline blending components without the use of noxious and/or corrosive liquid catalyst systems.

Allowed U.S. application Ser. No. 07/883,684, filed Feb. 11, 1992 now U.S. Pat. No. 5,191,150 discloses a method for decreasing the cloud-forming tendency of HF comprising adding a controlled amount of sulfolane to the HF. The application further discloses that conjunct polymeric byproducts (also referred to as acid soluble oil or ASO) accumulate in the liquid acid catalyst mixture and must be removed. The ASO, a complex mixture of polymers, is difficult to separate from mixtures of sulfolane and HF because the ASO contains components having boiling points which bracket the boiling point of sulfolane. The process solves this purification problem by removing (stripping) HF from the mixture to provide an intermediate stream containing less than about 30 weight percent HF. Below about 30 weight percent HF, the sulfolane/ASO mixture readily separates into a less-dense ASO-enriched liquid phase and a more-dense sulfolane-enriched phase. The gravitational separation step depends upon effective upstream HF removal. Because the known processes for removing HF from the ASO/sulfolane mixture (e.g., stripping and fractional distillation) are subject to process upsets, it would be beneficial to provide a separation method which in independent of upstream operating variations. Further, it would be desirable to generate a purified sulfolane stream which can be recycled directly to an operating alkylation reactor without further processing.

SUMMARY OF THE INVENTION

This invention provides a method for separating conjunct polymers (ASO) from a mixture containing conjunct polymers (ASO), HF and sulfolane which method is independent of upstream process steps for removing HF. The present method operationally isolates the gravitational separation step from conventional upstream HF removal steps to improve reliability. Prior to the advent of the present invention, an upstream process upset could compromise the effectiveness of the two-phase gravitational separation step by raising the HF concentration in the gravitational separator above the level necessary to effect phase separation, thus converting the two immiscible liquid phases in the gravitational separator to a single liquid phase and disrupting catalyst regeneration. The method of this invention first guards the gravitational separator against excursions in HF concentration. Second, the method of the invention partitions ASO and sulfolane between a less-dense liquid phase and a more-dense liquid phase to an extent sufficient that no further sulfolane purification is typically required before recycling the sulfolane to the reactor of an HF/sulfolane-catalyzed isoparaffin-olefin alkylation process. Third, the method of the invention improves operator control over the water content of an HF/sulfolane catalyst for continuous isoparaffin-olefin alkylation.

The method of the invention comprises the steps of:

(a) contacting a mixture of conjunct polymers, sulfolane, and HF with a sorbent to selectively sorb HF and water from said mixture to evolve an intermediate product containing less than about 5 weight percent HF;

(b) charging said intermediate product to a gravitational separation zone;

(c) holding said intermediate product in said gravitational separation zone for time sufficient to evolve two at least partially immiscible liquid phases in said gravitational separation zone; and (d) withdrawing a less-dense phase enriched in conjunct polymers and a more-dense phase enriched in sulfolane from said gravitational separation zone.

The method of the invention preferably further comprises removing at least a portion of the HF from the mixture of conjunct polymers, sulfolane, and HF before charging the stream to the sorption step. In this preferred embodiment, the HF is preferably removed by stripping the mixture with a gas. Useful stripping gases include isoparaffins and normal paraffins which are gaseous under ambient conditions, as well as vaporized alkylate.

The selective sorbents useful in the method of the invention are preferably regenerable, that is, the materials preferably sorb HF and water under sorption conditions and then release the HF and water under regeneration conditions so that the sorbent can be reused. From a process standpoint, the sorbent need not be regenerable to be useful, but regenerable sorbents are preferred to minimize waste disposal costs.

The preferred sorbents for the present invention contain no alumina or silica, which may react with HF under certain sorption conditions. Similarly, the selective sorbents useful in the method of the invention are preferably essentially free of ions which are exchangeable in the presence of HF. Sorbents containing exchangeable ions tend to consume HF to produce stable fluoride salts. Thus activated carbon, poly-sulfone resins, and poly-vinyl alcohols are the more preferred sorbents. Poly-vinyl alcohols are particularly preferred due to their ability to effectively sorb both HF and water.

The sorption step of the invention produces a product stream containing a lower concentration of HF and water than the feed. The sorption zone can, in theory, be sized to remove any amount of HF and water from the feed, but, from a practical standpoint, is typically sized to decrease the feed HF concentration by about 50 weight percent. Greater reductions in HF concentration produce higher purity ASO and sulfolane phases in the downstream gravitational separation zone, and for this reason, reductions in HF concentration of as much as 70 or 90 weight percent may be preferred. If a stripping step precedes the sorption step, the stripped feed preferably contains less than about 5 weight percent HF, more preferably less than about 1 weight percent HF. Typical weight hourly space velocities in the sorption zone (based upon HF and water in the feed) range from about 0.001 to about 1 $hr^{-1}$. Temperature in the sorption zone is not critical, but typically falls within the range of from about 27° C. (80° F.) to about 100° C. (212° F.), more typically from about 32° C. (90° F.) to about 43° C. (110° F.).

While many forms of activated carbons are useful sorbents in the present invention, the activated carbons referred to as gas- or vapor-phase activated carbons are preferred. The gas-phase activated carbons, characterized by surface areas of from about 800 to about 1200$m^2$/g, are preferred because they are readily regenerable and are typically available as hard granules or formed pellets (for ease of handling and mechanical durability). The pore size of the gas-phase activated carbons is typically less than about 3.0 nm, and the surface area is typically about 1000 $m^2$/g. See generally *Handbook of Separation Process Technology* 651 (R. W. Rousseau ed. 1987), which is incorporated by reference as if set forth at length herein.

If a regenerable sorbent material is used, the sorbent is typically regenerated by first rinsing with a solvent to remove residual ASO and sulfolane, and then flowing a carrier gas through the sorption bed at elevated temperature to desorb hydrodrofluoric acid and water. While any suitable hydrocarbon solvent may be used, alkylate is readily available, and is therefore preferred. Regeneration temperatures for most useful sorbents fall within the range of from about 150° C. ($\approx$300° F.) to about 315° C. ($\approx$600° F.), and the carrier gas flow is typically maintained through the sorption bed until the effluent gas gas is essentially free of HF.

BRIEF DESCRIPTION OF THE DRAWING

The Figure is a simplified schematic diagram showing the major processing steps of the method of the invention.

EMBODIMENT

Referring now to the Figure, a slipstream of spent alkylation catalyst 10 flows from an operating HF/sulfolane catalyzed isoparaffin-olefin alkylation process unit (not shown) and enters primary distillation/stripping tower 20. Stripping gas, for example, isobutane, enters distillation/stripping tower 20 through line 22, carries stripped HF upwardly through the tower, and exits the primary distillation/stripping tower 20 via overhead line 26, and optionally flowing to an overhead cooler and accumulator (not shown).

The bottoms product withdrawn from the primary distillation/stripping tower is withdrawn from the tower through line 28 at tower temperature of about 300° F. The bottom stream may optionally be cooled to a temperature as low as about 100° F. before entering sorption unit 30.

Sorption unit 30 comprises at least two sorption beds contained in separate vessels (not shown). The vessels are piped and valved for parallel/swing operation so that at least one sorption bed can be on stream while at least one sorption bed is being regenerated. The sorption unit preferably contains three sorption beds so that one bed can be operational while a second bed is being regenerated and the third bed is on standby to avoid any interruption in operation when the process flow shifts for regeneration. To regenerate a sorption bed, the process flow (from line 28) is shifted to a second sorption bed and the first sorption bed is rinsed with a suitable solvent, e.g., alkylate. A dry, inert gas at a temperature of about 205° C. (400° F.) is then charged to the sorption bed until the effluent gas from the sorption bed is essentially free of HF. Nitrogen or isobutane are typically used, and isobutane is preferred because the HF-enriched isobutane can then be recycled to the alkylation reaction zone (not shown).

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLE 2-4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixture containing about 5 weight percent HF (Example 4) separates into two distinct liquid phases more completely, forming higher purity phases than the stripped mixtures containing 10 weight percent HF (Example 3) and 25 weight percent HF (Example 2). Each of the more-dense sulfolane-enriched phases generated in Examples 2-4 may, in some cases, require further purification to maintain alkylate product quality while continuously recycling the sulfolane-enriched phase to an operating HF alkylation reactor.

EXAMPLE 5

The HF/sulfolane/ASO sample of Example 5 has the following composition:
HF 62 wt. %
Sulfolane 27 wt. %
Isobutane 4 wt. %
Water 1-2 wt. %
ASO 3 wt. %
Balance to 100% other hydrocarbons. This mixture is a single liquid phase at 90° F. and 120 psig.

The sample is brought to atmospheric pressure and room temperature and most of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases. In Example 5, the two phases appear within several minutes of the HF concentration reaching about 2 wt. %.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains 82.8 wt. % ASO, 13.3 wt. % sulfolane, and the balance of salts.

EXAMPLE 6

The HF/sulfolane/ASO sample of Example 5 is charged to an upper section of a packed stripper tower having five theoretical stages. Dry isobutane, entering near the bottom of the tower, flows upwardly through the packed section, stripping HF from the HF/sulfolane/ASO mixture. The stripped HF/sulfolane/ASO mixture (the stripper bottoms product) contains the following:
HF 9.3 wt. %
Sulfolane 72 wt. %
ASO 18.7 wt. %.

The stripped HF/sulfolane/ASO mixture is then charged to a sorption vessel containing granular activated carbon having a surface area of about 1000 $m^2/g$ at a weight hourly space velocity of about 0.01 $hr^{-1}$ (based upon HF and water in the feed) and a temperature of about 38° C. (100° F.). The effluent stream from the sorption vessel (containing less than about 1 weight percent HF) flows to a gravitational separator where it separates into two distinct liquid phases. The more-dense sulfolane-enriched phase contains about 8 weight percent ASO.

EXAMPLE 7 AND 8

The apparatus of Example 6 is modified with the addition of a bypass line and valving so that the stripper bottoms product may be selectively charged to the sorption zone or directly to the gravitational separation zone. Examples 7 and 8 first repeat the procedure of Example 6, allowing the process to reach steady state. Periodic sampling during continuous operation shows the the more-dense sulfolane-enriched phase withdrawn from the gravitational separator to consistently contain about 6-8 weight percent ASO.

EXAMPLE 7

Example 7 illustrates the potential effects of a stripper upset in the absence of the sorption zone.

After steady state has been reached with the sorption zone in-line, valves in the bypass line are opened to shunt the total stripper bottoms product through the bypass line. The gravitational separator continues to form two distinct liquid phases, although the purity of both phases gradually decreases. The isobutane flow to the stripper tower is shut off and the stripper bottoms composition is periodically sampled and analyzed. HF concentration rises markedly in the stripper bottoms product; periodic analysis of the less-dense and more-dense phases shows that ASO and sulfolane partition less effectively between the two phases as the HF feed concentration rises.

EXAMPLE 8

The procedure of Example 7 is repeated. With no isobutane flowing to the stripper tower and no liquid visible interface present in the gravitational separator, the valves in the sorption zone bypass are closed, charging the total stripper bottoms stream through the sorption zone at a weight hourly space velocity of less than about 0.1 based upon HF and water in the feed. After about one (1) gravitational separator volume flows through the sorption zone, a liquid-liquid interface appears in the gravitational separator and partitioning of ASO and sulfolane improves with time as steady state operation is achieved.

EXAMPLES 9-11

Examples 9-11 demonstrate the effectiveness of three sorbents for removing HF and water from feedstreams containing HF, sulfolane, and water. Each solid is added to a mixture of HF, sulfolane and water and then each mixture is sampled after 48 hours. The results are shown in the Table below.

TABLE

| Example Number | 9 | 10 | 11 |
|---|---|---|---|
| HF/Water (48/52 wt/wt), parts by wt | 1.00 | 1.00 | 1.3 |
| Sulfolane, parts by wt | 10.00 | 10.15 | 13.05 |
| Poly-sulfone resin, parts by wt | 2.01 | | |
| Poly-vinyl alcohol, parts by wt | | 1.95 | |
| Activated carbon, parts by wt | | | 2.55 |
| Original Percentages (weight) | | | |
| HF | 4.36 | 4.30 | 4.35 |
| Water | 4.73 | 4.66 | 4.71 |
| Final Percentages (weight) | | | |
| HF | 4.03 | 3.59 | 3.79 |
| Water | 4.80 | 3.29 | 5.65 |

The poly-vinyl alcohol sorbent is most preferred because of its ability to sorb both water and HF. Water content in HF/sulfolane alkylation catalysts has been found to be an important operating variable, and the poly-vinyl alcohol not only sorbs HF to enhance sulfolane/ASO gravitational separation, but improves operational flexibility by effectively sorbing water as well.

Changes and modifications in the specifically described embodiments can be carried out without departing from the scope of the invention which is intended to be limited only by the scope of the appended claims.

What is claimed is:

1. A method for separating ASO from a mixture containing ASO, HF and sulfolane comprising the steps of:
   (a) contacting said mixture with a sorbent to selectively sorb HF and water from said mixture to evolve an intermediate product containing less than 5 weight percent HF;
   (b) charging said intermediate product to a gravitational separation zone;
   (c) holding said intermediate product in said gravitational separation zone for time sufficient to evolve two at least partially immiscible liquid phases in said gravitational separation zone; and
   (d) withdrawing a less-dense phase enriched in ASO and a more-dense phase enriched in sulfolane from said gravitational separation zone.

2. The method of claim 1 further comprising stripping HF from said mixture before said sorption step (a).

3. The method of claim 1 wherein said selective sorbent contains essentially no silica.

4. The method of claim 1 wherein said selective sorbent contains essentially no alumina.

5. The method of claim 1 wherein said selective sorbent contains essentially no ions which are exchangeable in the presence of HF.

6. The method of claim 1 wherein said intermediate product stream contains less than 1 weight percent HF.

7. The method of claim 1 wherein said mixture contacts said sorbent at weight hourly space velocity of from about 0.001 to about 1 hr$^{-1}$ based upon HF and water in the mixture.

8. The method of claim 1 wherein said solid sorbent is selected from the group consisting of activated carbon, poly-vinyl alcohols, and poly-sulfone resins.

* * * * *